United States Patent [19]

Rashtchian et al.

[11] Patent Number: 4,785,086

[45] Date of Patent: Nov. 15, 1988

[54] TEST FOR CAMPYLOBACTER

[75] Inventors: Ayoub Rashtchian, Northboro; Renee Fitts, Framingham, both of Mass.

[73] Assignee: Integrated Genetics, Inc., Framingham, Mass.

[21] Appl. No.: 692,778

[22] Filed: Jan. 17, 1985

[51] Int. Cl.$^4$ .................. C07H 21/00; C12Q 1/68; C12N 1/00; C12N 1/20

[52] U.S. Cl. .................. 536/27; 435/6; 435/172.3; 435/320; 435/253; 935/78; 935/72

[58] Field of Search .................. 435/6, 7, 29, 34, 35, 435/253, 317, 803, 822, 172.3; 436/63, 94, 501, 518, 530; 536/27; 935/6, 9, 72, 78

[56] References Cited

U.S. PATENT DOCUMENTS 4,358,535 11/1982 Falkow et al. ............... 436/504 X

FOREIGN PATENT DOCUMENTS 114668 8/1984 European Pat. Off. .

OTHER PUBLICATIONS

Leaper, S. et al, *FEMS Micro. Lett.*, vol. 15, 1982, pp. 203–208..
Owen, J. *Eur. J. Clin. Micro.*, vol. 2, No. 4, Aug. 1983, pp. 367–377.
Nilsson et al., (1983) Nuc. Acids Res. 11(22):8019.

Fitts et al. *Applied and Environ. Microbiol.* 46:1146–1151, Nov. 1983.

*Primary Examiner*—Charles F. Warren
*Assistant Examiner*—Jeremy M. Jay

[57] ABSTRACT

A DNA probe and method for detecting *Campylobacter jejuni*, which consists essentially of a DNA sequence that is:

(a) derived from a chromosomal sequence of a bacterium of the species *C. jejuni* or *C. coli* but is less than the entire chromosomal sequence of that bacterium;

(b) capable of hybridizing to DNA of at least 80% of bacteria that are in the species *C. jejuni* and/or *C. coli;* and (c) not capable of hybridizing to DNA of bacteria that are not in the genus Campylobacter. The method features detecting *C. jejuni* in a sample by providing at least one probe capable of selectively binding to *C. jejuni* but not bacteria that do not belong to the genus Campylobacter, contacting that DNA probe with bacteria in the sample under conditions that allow the probe to hybridize to *C. jejuni* in the sample thus forming hybrid DNA complexes, and detecting the hybrid complexes as an indication of *C. jejuni* in the sample.

4 Claims, No Drawings

TEST FOR CAMPYLOBACTER

BACKGROUND OF THE INVENTION

This invention relates to detecting bacteria of the species *Campylobacter jejuni* and *Campylobacter coli*. Throughout this application, when we refer to bacteria of the genus *Campylobacter* or of the species *C. ejuni, C. coli*, or *C. fetus* (or simply "*C. jejuni*", "*C. coli*", or "*C. fetus*", respectively) we mean bacteria that are so classified in Skerman et al. (1980) "Approved List of Bacterial Names" Int. J. Syst. Bacteriol. 30:225-420. By "*C. jejuni*", we mean to include bacteria described as *C. fetus* subsp. *jejuni* (but not other members of the species *C. fetus*) in Buchanan et al., *The Shorter Bergey's Manual for Determinative Bacteriology* (Williams & Wilkins 1982) in accordance with the classification in Skerman, supra and with the classification in a more recent edition of Bergey's Manual of Systematic Bacteriology (9th ed. 1984, vol. 1).

Detection of *C. jejuni* and *C. coli* is important in various medical contexts. For example, the presence of *C. jejuni* or *C. coli* in stool samples is indicative of gastroenteritis, and the ability to screen for their presence is useful in treating and controlling that disease. Detection of *C. jejuni* and *C. coli* in any possible transmission vehicle such as food is also important to avoid the spread of gastroenteritis.

Currently, the presence of *C. jejuni* and *C. coli* in stool samples is detected by cultivating an appropriately prepared sample on microbiological media under conditions favorable for growth of those bacteria. Those conditions include reduced oxygen tension and a temperature of about 42° C. The resulting colonies are then examined for morphological and biochemical characteristics, a process that typically takes at least three days and does not permit processing large numbers of samples.

Taber et al. U.S. Ser. No. 529,031 filed Sept. 2, 1983 discloses DNA probes for determining the presence of bacteria of the genus Salmonella in food.

Falkow U.S. Pat. No. 4,358,535 discloses a DNA probe for detecting Enterotoxigenic *E. coli* in clinical specimens.

SUMMARY OF THE INVENTION

In one aspect, the invention features a DNA probe consisting essentially of a DNA sequence that is:

(a) derived from a chromosomal sequence of a bacterium of the species *C. jejuni* but is less than the entire chromosomal sequence of that *C. jejuni*;

(b) capable of hybridizing to DNA of at least 80% of bacteria that are in the species *C. jejuni*; and (c) not capable of hybridizing to DNA of bacteria that are not in the genus Campylobacter. By a sequence that is "derived from a chromosomal sequence", we mean a sequence that is identical to that sequence, or a natural or engineered or synthetic variant that retains the desired function.

In another aspect, the invention features a method of detecting *C. jejuni* in a sample by providing at least one probe capable of selectively binding to DNA of *C. jejuni* but not to DNA of bacteria that do not belong to the genus Campylobacter, contacting that DNA probe with bacteria in the sample under conditions that allow the probe to hybridize to *C. jejuni* in the sample thus forming hybrid DNA complexes, and detecting the hybrid complexes as an indication of *C. jejuni* in the sample.

In a third aspect, the probe sequence is derived from, but is less than, an entire chromosomal sequence of *C. coli*, and it is capable of hybridizing to at least 80% of the bacteria of that species.

In preferred embodiments of the first aspect of the invention, the probe is also capable of binding to at least 80% of bacteria that are in the species *C. coli*. Most preferably in all aspects of the invention, the probe is capable of binding to at least 90% of the *C. jejuni* and 90% of the *C. coli*) so that it is used to detect the presence of either *C. jejuni* or *C. coli* in any given sample. Also in preferred embodiments, the probe is a HindIII fragment of a chromosome of a bacteria from the species *C. jejuni* or *C. coli*. The probe may be labeled using a label that is detectable, for example, a radioactive isotope such as $^{32}P$ or $^{125}I$ incorporated in the probe by nick-translation or other means of labeling; alternatively the label binds selectively to an indicator comprising a binding partner and a chemical entity detectable, e.g. by fluorometric, immunological, electron microscopic or enzymatic methods. The label/binding partner pair may be avidin and biotin.

In preferred embodiments of the method, before contacting the probe with the bacterial DNA, the bacteria are separated from the sample and lysed to release their DNA, which then is denatured and immobilized on a binding support such as a nitrocellulose membrane. The sample may be food or a diagnostic sample, e.g. a stool sample. The probe also may be unlabeled, in which case the contacting and detecting steps are performed by sandwich hybridization (referred to in more detail below). One or more probes may be used in the method to increase its sensitivity.

In a fourth aspect, the invention features a DNA probe consisting essentially of fragments representing a total DNA preparation of *C. jejuni*, no detectable percentage of which is capable of hybridizing to bacteria that are not in the genus Campylobacter; a detectable percentage of the fragments will hybridize to the DNA of any given member of that genus. By the phrase "total DNA preparation," I mean DNA isolated by severing the chromosomal DNA to create various fragments that collectively represent substantially the entire chromosomal sequence. The DNA probe is used in a method comprising isolating fragments representing a total DNA preparation of *C. jejuni* and exposing the fragments to DNA of bacteria from a sample under conditions that allow hybridization.

In preferred embodiments of the fourth aspect, the *C. jejuni* used for the total DNA preparation is strain N941 (ATCC 39983), and the probe fragments are labeled.

The probe and detection method provide a reliable, fast, and straightforward means for detecting *C. jejuni* and *C. coli*—the two species of Campylobacter primarily implicated in gastroenteritis. So far as the inventors are aware, the probe does not depend on the ability to match a DNA probe with bacteria that e.g., express a specific protein, are pathenogenic, or possess any other phenotypical characteristic. Thus, the selectivity and utility of the probe is not limited to members of the species that exhibit a specific characteristic; nor is it dependent on locating the DNA responsible for a characteristic.

Our discovery that there is not just one, but a number, of specific probes provides the added advantage of increased sensitivity and signal amplification; the larger the number of different probes used, the greater the sensitivity of the assay. This is because when several different probes are used, each can hybridize to a different portion of a single bacterial chromosome so that the single chromosome bears multiple labels.

The assay of the invention gives rapid, accurate results. A fast and definitive result is important when determining a patient's therapeutic regime. When the detection method is used for food samples, its speed allows food manufacturers to reduce food storage time prior to shipment. In addition, the short time required to complete the test permits laboratories to handle large numbers of samples in a short period of time. Furthermore, the assay, depending only on the overall DNA sequences of the bacteria rather than their biochemical properties, can detect biochemically atypical as well as typical bacteria so that false negatives are avoided. The test requires no elaborate equipment and can be performed easily by personnel who have not had extensive technical training.

Finally, the recognition that it is possible to use a total DNA preparation without detectable hybridization to non-Campylobacter bacteria enables a ready source of easily prepared probes. A large number of fragments of the total DNA preparation can be expected to hybridize to any Campylobacter bacteria, providing extremely high sensitivity to such bacteria. Surprisingly, a total DNA preparation of *C. jejuni* does not provide false positive results, indicating that no detectable percentage of the chromosomal fragments hybridize to non-Campylobacter, and indicating that the amount of DNA homology between *C. jejuni* and other groups of bacteria is negligible.

Other features and advantages of the invention will be apparent from the following description of the preferred embodiments thereof and from the claims.

DESCRIPTION OF THE PREFERRED EMBODIMENTS

Isolation of Probes.

A genomic library of *C. jejuni* DNA is constructed in a suitable plasmid or phage vector. A number of suitable vectors are available and have been described in Maniatis et al. (1982) *Molecular Cloning*, Cold Spring Harbor Laboratory. One such vector is pUN121 [Nilsson et al. (1983) Nucleic Acids Research 11:8019–8030]. The DNA from *C. jejuni* N941 (ATCC 39983) is digested with restriction endonuclease HindIII, creating fragments of different sizes. These fragments are then ligated into the HindIII site of a suitable vector using the general method described in Cohen et al., (1973) Proc. Nat'l Acad. Sci. 70:3240. This ligation mix is then used to transform *E. coli* HB101. The transformants are selected on the basis of a suitable marker. For example, when using the plasmid pUN121, the transformants can be selected on the basis of resistance to tetracycline. The transformants are then screened for the presence of plasmid DNA and independent transformants are examined by agarose gel electrophoresis. The plasmid DNA is transferred onto nitrocellulose membrane filters by the method of Southern described in Maniatis et al. (1982) cited above; and the DNA is probed with nick-translated *E. coli* DNA. The plasmids which do not hybridize to *E. coli* DNA (about 95%) are selected and purified by CsCl-ethidium bromide gradients. The insert DNA is purified from agarose gels after digestion with HindIII. These individual DNA fragments are then labeled with nick-translation and used as probes in testing *C. jejuni* or *C. coli* strains and also, enteric bacteria often found in feces as part of normal flora or as pathogens. Table 1 exemplifies the types of non-Campylobacter enteric bacteria that may be tested.

TABLE 1

| ENTERIC BACTERIA USED IN SCREENING | |
|---|---|
| *Escherichia coli* | *Salmonella enteritidis* |
| *Enterobacter cloacae* | *Salmonella serotype* Cl |
| *Enterobacter agglomi* | *Salmonella typhimurium* |
| *Enterabacter gergoviae* | *Serratra liquefaciens* |
| *Citrobacter forundii* | *Serratia marcescens* |
| *Citrobacter diversus-levihea* | *Shigella flexneri* |
| *Klebsiella pneumoniae* | *Shigella sonneii* |
| *Klebsiella oxytoca* | *Shigella byoydii* |
| *Proteus mirabilis* | *Shigella dysenteriae* |
| *Proteus morganii* | *Vibrio parahaemolyticus* |
| *Proteus rettgeri* | |

Strains of *C. jejuni* and *C. coli* that can be used in the above screening procedure are available from numerous sources, particularly from major medical centers. For example, well-characterized *C. jenjuni* and *C. coli* strains are available from the University of Massachusetts Medical Center in Worcester, Mass. c/o Gary Doren.

*C. jejuni* and *C. coli* strains are also available from Scott Laboratories, Inc., Fiskville, Rhode Island. In addition, various clinically isolated strains are available from Scott Laboratories. Other sources of clinical isolates include the Veterans Administration Medical Center, Denver, Colorado (M. J. Blaser) and Vermont Department of Public Health, Burlington, Vermont (Tanya Sandros).

By way of example, Table 2 lists eight specific probes identified by their inability to hybridze with DNA of the species listed in Table 1 and their ability to hybridize with a high precentage of 98 distinct Campylobacter strains.

TABLE 2

| LIST OF CAMPYLOBACTER SPECIFIC PROBES AND THEIR PROPERTIES | | |
|---|---|---|
| Probe | Size(b) | Percentage of Strains Detected |
| CJ12A | 960 | 100% |
| CJ29B | 970 | 85% |
| CJ41A | 2150 | 91% |
| CJ41B | 2 fragments: 1250 and 1300 b.p. | 93% |
| CJ44A | 2 fragments: 2650 and 3000 b.p. | 99% |
| CJ44B | 1700 | 99% |
| CJ59 | 1500 | 90% |
| CJ87A | 1200 | 96% |

The four preferred probes have been deposited with the NRRL located in Peoria, Illinois and bear the following accession numbers

| Probe | NRRL No. |
|---|---|
| CJ12A | B 15911 |
| CJ29B | B 15912 |
| CJ59 | B 15913 |
| CJ87A | B 15914 |

With respect to these probes and the above-mentioned ATCC deposit of *C. jejuni*, N941, applicants' assignee, Integrated Genetics, Inc., acknowledges its responsibility to replace these cultures should they die before the end of the term of a patent issued hereon, and its responsibility to notify the depository of the issuance of such a patent, at which time the deposits will be made available to the public Applicants' assignee, Integrated Genetics, Inc., agrees (1) to replace the cultures if they should die or be destroyed during the duration of the deposit (2) upon issuance of a patent, to remove irrevocably all restrictions to access to the cultures by legally entitled parties for the duration of the deposit and; (3) to maintain the cultures for 5 years after the last request for a culture, for the life of the patent, or for 30 years, whichever is the longer. Until that time the deposits will be made available to the Commissioner of Patents under the terms of 37 CFR Section 1.14 and 35 USC Section 112.

Construction, Labeling, and Use of Probes.

Probes may be constructed from the isolates of Table 2 as described by Taber and Fitts, U.S. Ser. No. 529,031, filed Sept. 2, 1983, which is hereby incorporated by reference. DNA is labeled by nick-translation according to known methods or by other known methods of labeling such as primer extension, or by the non-isotopic methods described by Landes U.S. Ser. No. 529,044 filed Sept. 2, 1983, which is hereby incorporated by reference. U.S. Ser. No. 529,031 and U.S. Ser. No. 529,044 also describe apparatus and methods for the use of probes that have been so labeled. Specifically, those skilled in the art will recognize that it is possible to adjust hybridization conditions such as temperature (e.g. 55°–70° C.) ionic strength (1M NaCl), and other factors (e.g. the addition of formamide) provide selectivity and sensitivity levels.

Detection of C. Jejuni in Stools

Stool samples from healthy individuals may be screened with each of the DNA probes CJ12A, CJ29B, CJ44A, CJ59 and CJ87A and also using a mixture of probes. The hybridization may be performed as described in the above-referenced U.S. Ser. No. 529,031 on stool samples which are directly spotted on nitrocellulose membrane filters as well as samples which are inoculated on selective plates as described by Blaser et al., (1979) Ann. Intern. Med. 91:179 and on non-selective plates. In all cases, the stool from healthy individuals shows no hybridization to the DNA probes, confirming previous studies showing that healthy individuals do not have any detectable $C.$ $jejuni$ in their stools. (M. B. Skirrow, 1982, J. Hyg. Camb., 89:175). Stool specimens that include $C.$ $jejuni$ are detectable in the stool samples. When radioactivity labeled probes are used to evaluate samples immobilized on filters, exposure of the filters to X-ray film will exhibit a dark spot for samples containing $C.$ $jejuni$ or $C.$ $coli$.

Total DNA Probe

An extraordinarily sensitive DNA probe can be prepared from the DNA of a member of the species $C.$ $jejuni$. Specifically, a total DNA preparation is produced from a strain of $C.$ $jejuni$ such as N941, discussed above. Any of a number of known techniques may be used for that purpose. For example, Maniatis, cited above, cites suitable procedures for isolating bacterial DNA. These isolation procedures fragment the bacterial chromosome which is about 4,000 k.b. (assuming that the $E.$ $coli$ and $C.$ $jejuni$ chromosomes are comparable in size) to yield isolated fragments of about 10–20 kb. These fragments are then labeled by any of the procedures discussed above such as nick translation, further fragmenting the DNA to an average size of about 500–1000 bp. These fragments are a suitable size for a probe and, surprisingly, they exhibit no detectable hybridization with non-Campylobacter when subjected to the hybridization procedures discussed above. At the same time, the probe is extremely sensitive because hybridization can take place at many locations on the same Campylobacter chromosome due to the presence of numerous distinct labeled fragments.

Other Embodiments

Other embodiments are within the following claims. For example, other labeling methods may be used. Unlabeled probes may be used, in which case a sandwich hybridization is used according to known techniques such as the one described in European Patent Application EPO 079139A1. The number of probes required depends in part on the sensitivity required in a given application and the tolerance for false negative results. In general, one or more probes may be used. Synthetically constructed DNA sequences as well as pieces of the genome of naturally occurring $C.$ $jejuni$ or $C.$ $coli$ can be used as probes.

Other clinical samples may be tested—for example, gastric juices or intestinal contents. Food may be tested as described in Taber and Fitts U.S. Ser. No. 529,031 cited above.

We claim:

1. A DNA probe consisting essentially of a DNA sequence from the plasmid present in:
   (a) CJ12A (NRRL 15911);
   (b) CJ29B (NRRL 15912);
   (c) CJ59 (NRRL 15913); or
   (d) CJ87A (NRRL 15914);
wherein said DNA sequence hybridizes under hybridizing conditions to DNA of at least 80% of bacteria in the species *Campylobacter jejuni*, and not to non-Campylobacter species.

2. A DNA probe mixture consisting essentially of at least two probes according to claim 1.

3. A DNA probe mixture consisting essentially of at least three of the probes according to claim 1.

4. A DNA probe mixture consisting essentially of probes (a), (b), (c), and (d) according to claim 1.

* * * * *

UNITED STATES PATENT AND TRADEMARK OFFICE
CERTIFICATE OF CORRECTION

PATENT NO. : 4,785,086

DATED : November 15, 1988

INVENTOR(S) : Ayoub Rashtchian et al.

It is certified that error appears in the above-identified patent and that said Letters Patent is hereby corrected as shown below:

On the face of the patent, the following U.S. Patent Documents have not been cited:

4,486,539   12/84   Ranki et al.

4,563,419    1/86   Ranki et al.

The following Other Publications have not been cited:

Taylor, D.E., et al., Antimicrob. Agents and Chemother., Vol. 24, No. 6, 1983, pp. 930-935

Fennell, C.L. et al., J. Infect. Dis., Vol. 149 No. 1, 1984, pp. 58-66

Hebert, G.A. et al., J. Clin. Micro., Vol. 20, No. 1, 1984, pp. 138-140

Signed and Sealed this

Fifteenth Day of August, 1989

*Attest:*

DONALD J. QUIGG

*Attesting Officer*    *Commissioner of Patents and Trademarks*

UNITED STATES PATENT AND TRADEMARK OFFICE
CERTIFICATE OF CORRECTION

PATENT NO. : 4,785,086

DATED : November 15, 1988

INVENTOR(S) : Ayoub Rashtchian et al.

It is certified that error appears in the above-identified patent and that said Letters Patent is hereby corrected as shown below:

ON THE TITLE PAGE,

Under FOREIGN PATENT DOCUMENTS insert

-- 114,668   8/1/84   Europe --.

Signed and Sealed this

Twelfth Day of December, 1989

Attest:

JEFFREY M. SAMUELS

Attesting Officer

Acting Commissioner of Patents and Trademarks